United States Patent [19]

Ohira et al.

[11] Patent Number: 4,734,320
[45] Date of Patent: Mar. 29, 1988

[54] STRETCHABLE CLOTH ADHESIVE TAPE

[75] Inventors: Osamu Ohira; Katsuo Matsumoto; Hiroshi Doi; Seishi Suzuki; Eiji Tsukahara, all of Osaka, Japan

[73] Assignee: Nitto Electric Industrial Co., Ltd., Osaka, Japan

[21] Appl. No.: 8,724

[22] Filed: Jan. 30, 1987

[30] Foreign Application Priority Data

Apr. 24, 1986 [JP] Japan .................................. 61-96442

[51] Int. Cl.⁴ ..................... A61F 13/00; A61F 15/00; A61L 15/00; C09U 7/02
[52] U.S. Cl. .................................... 428/231; 128/155; 128/156; 428/261; 428/343; 428/257; 156/160; 156/163
[58] Field of Search ................ 128/155, 156; 428/231, 428/261, 343, 703; 156/160, 163

[56]  References Cited

U.S. PATENT DOCUMENTS

| 2,957,512 | 10/1960 | Wade et al. .......................... 156/163 |
| 3,728,203 | 4/1973 | Taylor ............................. 156/160 X |
| 3,888,247 | 6/1975 | Stenvall ................................ 128/155 |
| 4,366,814 | 1/1983 | Riedel ................................ 128/156 |
| 4,424,808 | 1/1984 | Schöfer ............................... 128/156 |
| 4,488,928 | 12/1984 | Ali Khan et al. ............... 156/160 X |
| 4,510,197 | 4/1985 | Shah ................................ 128/155 X |
| 4,561,434 | 12/1985 | Taylor ............................. 128/155 X |
| 4,604,315 | 8/1986 | McCall et al. .................. 128/156 X |
| 4,606,964 | 8/1986 | Wideman ........................ 156/163 X |
| 4,631,227 | 12/1986 | Nakamura ........................ 128/156 X |

Primary Examiner—George F. Lesmes
Assistant Examiner—D. R. Zirker
Attorney, Agent, or Firm—Sughrue, Mion, Zinn, Macpeak, and Seas

[57]  ABSTRACT

A stretchable cloth adhesive tape useful for taping which comprises a tape support woven from warps and wefts and having stretchability in at least one direction and a pressure-sensitive adhesive layer formed on one surface of the support. The tape support is fixed in a state stretched at least 3% of its maximum elongation upon being stretched to a limit.

13 Claims, 1 Drawing Figure

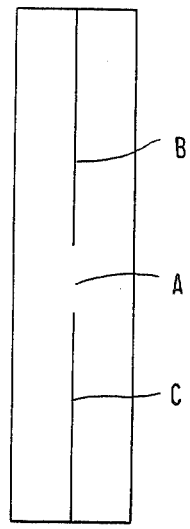

STRETCHABLE CLOTH ADHESIVE TAPE

FIELD OF THE INVENTION

This invention relates to a stretchable cloth adhesive tape applied mainly to a human body surface. More specifically, it relates to a stretchable cloth adhesive tape which is applied to a body surface to prevent excessive stretching or contraction of muscles between their origin and termination or to promote blood flow in the part of the muscles at which contracture occurs so as to permit normal energy metabolism.

BACKGROUND OF THE INVENTION

When a disease occurs at a joint portion of the knees, thighs, elbows, shoulders, etc., it is the general practice to apply a plaster of Paris bandage or a supporter or a stretchable adhesive tape in order to fix that portion.

A conventional stretchable cloth adhesive tape used in a taping operation is produced by forming a pressure-sensitive adhesive layer on a release liner such as a release paper or a release film in advance, superimposing a tape support delivered under substantially no stretch on the adhesive layer, press-bonding these by, for example, passing them between rollers, and winding up the assembly in a roll form while the release liner is left there, or winding up the tape support in a roll form after the liner has been peeled off, because it is difficult to form the pressure-sensitive adhesive layer directly on the stretchable tape support.

The stretchable cloth adhesive formed in a roll form, for example, without applying stretching to the tape support has the advantage that a wide range of stretch ratios can be obtained from the start to the end of stretching, and the user can perform taping by imparting the desired stretch On the other hand, since the range of stretch ratios is too wide, the stretch of the tape may vary locally depending upon the manner of exerting a force during taping. This brings about the defect that the function of the tape to prevent stretching or contraction of the muscles cannot be obtained, or can be obtained only non-uniformly.

Furthermore, even when the pressure-sensitive adhesive layer and the tape support are press-bonded between rolls, etc., the state of adhesion at the interface of those is insufficient. Hence, when the tape support absorbs water after taping, the tape support might be peeled from the pressure-sensitive adhesive layer.

SUMMARY OF THE INVENTION

Accordingly, one object of this invention is to provide a stretchable cloth adhesive tape having a narrow range of elongations in which the elongation of the tape support is controlled.

Another object of this invention is to provide a stretchable cloth adhesive tape which has high adhesion strength between the tape support and the pressure-sensitive adhesive layer.

These objects of this invention are achieved by a stretchable cloth adhesive tape comprising a tape support woven from warps and wefts and having stretchability in at least one direction and a pressure-sensitive adhesive layer formed on one surface of the support, the tape support being fixed in a state stretched at least 3% of its maximum elongation upon being stretched to a limit.

BRIEF DESCRIPTION OF THE ACCOMPANYING DRAWING

The drawing is a front view of a tape piece obtained by punching out from the stretchable cloth adhesive tape obtained in Example 1.

DETAILED DESCRIPTION OF THE INVENTION

The term "limit", as used in the specification and the appended claims, means that the tape support is about to break when a stress is applied thereto. The term "maximum elongation" means the elongation of the tape support immediately before its breakage.

The tape support used in this invention is composed of a woven cloth woven from warps and wefts and having stretchability in one or two directions or in an oblique direction, in which the warps and/or wefts are formed of stretchable yarns.

For the purpose of illustration, a tape support having stretchability only in one direction will be described. The tape support having stretchability in one direction only is generally given stretchability only in the longitudinal direction, namely in the warp direction. In this case, the tape support is generally non-stretchable in the widthwise direction, i.e., in the weft direction.

The warps may be composed of yarns made of a material having stretchability, or of yarns made from a non-stretchable material but having been subjected to a stretching treatment typified by crimping.

The material having stretchability is, for example, a material having an elongation of 50 to 800%, such as a synthetic rubber (e.g., polyurethane rubber or chlorinated rubber), or a synthetic resin (e.g., a mixture of polypropylene and ethylene/vinyl acetate copolymer). These materials are used in the form of mono- or multifilaments having a size of about 20 to 250 denier, preferably 40 to 150 denier.

The above-mentioned mono- or multifilaments may be used singly as the stretchable yarns consituting the warps. It is also possible to use composite yarns obtained by using these filaments as a core, and covering the core tightly with natural and/or synthetic yarns having an elongation of 50% or less and a size of 100 to 500 denier. When a tension in the warp direction is exerted on a stretchable cloth adhesive tape obtained by using a tape support comprising such composite yarns as warps, the covering yarns wrapped closely about the core filaments turn spirally as the core is stretched and give a stretch to the tape. At the same time even when the core can still stretch, the stretch of the tape is restrained as a result of the deformation of the covering yarns to its maximum point.

If, at this time, the core is colored differently from the covering yarns or the wefts, the color of the core can be visually observed from the surface of the tape as the covering yarns closely contacting with each other become spiral and thus are spread. Since the color of the core changes in shade according to its stretch ratio, the tape can be applied with a predetermined elongation by visual observation if the color corresponding a right elongation is prescribed.

The count of the warps is determined depending upon the denier size of the yarns. The count is generally 15 to 50/inch, preferably 20 to 40/inch. If it is less than 15/inch, the contracting force of the tape after stretching is too small. If it exceeds 50/inch, this contracting force is too large. Hence, counts outside the specified range are not desirable.

The wefts are yarns of natural and/or synthetic fibers having a denier size of 100 to 500 denier. The count of the wefts is generally 20 to 100/inch.

The yarns of natural fibers include yarns of plant fibers typified by cotton and yarns of animal fibers typified by wool. The synthetic fiber yarns include yarns of regenerated fibers typified by viscose rayon, yarns of semisynthetic fibers typified by acetates, yarns of synthetic fibers typified by polyamides, polyesters and polyolefins, and yarns of inorganic fiber typified by glass fibers.

A pressure-sensitive adhesive layer is formed on one surface of the tape support constructed in the manner described above to form the stretchable cloth adhesive tape of this invention.

Preferably, the pressure-sensitive adhesive layer is formed, for example, by stretching the tape support to an extent of at least 3%, preferably 5 to 80%, more preferably 10 to 50%, of its maximum elongation when it is stretched to the limit, superimposing it on the surface of a release liner on which a pressure-sensitive adhesive solution having a designed viscosity is coated, and thereafter drying the assembly under heat or cooling it. When the stretched tape support is superimposed on the adhesive in solution as described above, part of the adhesive bites into the surface layer of the support. The adhesive solidifies in this state, and the tape support is fixed by the adhesive while it is in the stretched state. At the same time, the adhesion strength between the tape support and the pressure-sensitive adhesive layer is increased.

Alternatively, a stretchable cloth adhesive tape having high adhesion strength can be obtained by superimposing the tape support to which a stretch has been given on a layer of a hot-melt pressure-sensitive adhesive formed, on a release liner, and pressing the assembly under heat whereby the tape support is fixed by the adhesive while it is in the stretched state.

If the pressure-sensitive adhesive layer is formed by stretching the tape support to an extent of less than 3% of its maximum elongation, the elongation range of the tape at taping is so great that the elongation tends to become ununiform.

The pressure-sensitive adhesive layer may be a rubber-type adhesive comprising a rubber such as a natural or synthetic rubber and tackifier resins, or a synthetic resin-type adhesive typified by an acrylic adhesive composed of a copolymer of an acrylic ester and a copolymerizable monomer. It may be in the form of an aqueous dispersion, a solvent-base adhesive or a solventless adhesive. When the pressure-sensitive adhesive is brought into contact with the tape support while it is in the form of a liquid, the adhesive liquid preferably has a viscosity, measured by a BH-type rotary viscometer, of 300 to 800 poises (at 25° C., solids content 25–40% by weight). It is preferable to impart air permeability to the pressure-sensitive adhesive layer formed on the tape support because it permits prevention of any trouble which may occur when the space between the tape applied and a body surface becomes stuffy. Air permeability may be imparted by subjecting the adhesive layer to a physical or chemical treatment.

The tape support in the resulting stretchable cloth adhesive tape is fixed in the stretched state to the pressure-sensitive adhesive layer. If the properties of the tape support and the properties and thickness of the pressure-sensitive adhesive layer are properly prescribed so that a stress at 20% stretch on the tape will be at least 250 g/19 mm (at 25° C.), preferably 300 to 1800 g/19 mm (at 25° C.), a stress sufficient to fix muscles can be obtained at the time of taping by giving only a relatively small stretch to the tape.

Since the stretchable tape support in the stretchable cloth adhesive tape of this invention is fixed while being stretched at least 3%, preferably 5 to 80%, of the maximum elongation when it is stretched to the limit, the stretching width of the tape is much restricted as compared with the tape support and the elongation of the tape varies only within a narrow range. Thus, taping can be performed uniformly. Furthermore, since taping is performed by further stretching the tape which has been previously fixed in the stretched state, taping can be effected at a low stretch ratio, and after taping, a uniform fixing effect can be obtained. Moreover, since a part of the pressure-sensitive adhesive layer bites into the tape support, the adhesion strength between them is high.

The following examples illustrate the present invention more specifically. It should be understood that the invention is in no way limited to these examples.

EXAMPLE 1

A tape support (elongation 60%) was made from a woven fabric composed of wooly nylon yarns having a size of 70 denier and an elongation of 90% as wefts with a count of 32/inch and mixed yarns of cotton and polyester having a size of 130 denier as wefts with a count of 80/inch.

Separately, 2-ethylhexyl acrylate and acrylic acid in a weight ratio of 95:5 were polymerized in ethyl acetate by conventional manner to prepare a pressure-sensitive adhesive solution having a viscosity of about 450 poises (at 25° C.; solids content 33% by weight).

A release sheet was used which was obtained by laminating polyethylene to the surface of kraft paper and coating a silicone-type releasing agent on the polyethylene coat. The adhesive solution was coated on the releasing agent layer of the release sheet and the tape support was superimposed on the coated layer while being stretched about 30%. The assembly was passed between rolls to press-bond the two layers. The bonded assembly was passed through a drying oven kept at about 140° C. at a rate of 10 m/min. to obtain a stretchable cloth adhesive tape in accordance with this invention.

The elongation of this tape was about 30%, and its stress at 20% stretch was 420 g/19 mm. The tape was punched out into a piece as shown in the accompanying drawing, and applied to the elbow along the biceps brachii while the elbow joint was bent at an angle of about 135°. Specifically, the central portion A of the tape was applied to the elbow joint, and the upper part of the tape was then applied to the lower end portion of the biceps brachii with the cut B opened at an angle of about 30°. Furthermore, the lower part of the tape was applied by opening the cut C at an angle of about 70° and stretching the tape to a maximum extent while the elbow joint was stretched. After completion of taping in this manner, a good fixed feeling was obtained.

For comparison, the above pressure-sensitive adhesive solution was coated on the release sheet and dried to form a film. The above tape support was superimposed on the film without substantial stretching, and the assembly was bonded to form a stretchable cloth adhesive tape. The resulting tape had an elongation of about 60%, and a stress at 20% stretch of 245 g/19 mm. When this tape was used in taping as described above, its contracting force was weak, and its stretch was non-uniform. Hence, no good fixed feeling could be obtained.

The two tapes were each immersed in water at 20° C. for 1 hour and then stretched. No peeling between the tape support and the pressure-sensitive adhesive layer was seen in the tape of this invention. However, the tape prepared for comparison was readily delaminated between the support and the adhesive layer.

EXAMPLE 2

Composite yarns obtained by covering a polyurethane rubber core (elongation 600%) with fiber yarns closely wrapping about the core were used as the wefts, and tape supports shown in Table 1 were produced. Using the tape supports, stretchable cloth adhesive tapes were obtained by the same operation as in Example 1. The results obtained are shown in Table 1.

TABLE 1

|  | Sample No. | | | |
| --- | --- | --- | --- | --- |
|  | 1 | 2 | 3 | 4 |
| Tape Support | | | | |
| Warps: | | | | |
| Core size (denier) | 70 | 40 | 120 | 30 |
| Covering yarns | PET:Cotton = 3:7 | Cotton | Cotton | Cotton |
| Size of the covering yarns (denier) | 250 | 250 | 250 | 250 |
| Count (per inch) | 30 | 30 | 33 | 40 |
| Wefts: | | | | |
| Material | PET:COTTON = 3:7 | Cotton | Cotton | Cotton |
| Size (denier) | 250 | 300 | 300 | 300 |
| Count (per inch) | 50 | 40 | 60 | 40 |
| Elongation (%) | 130 | 80 | 190 | 50 |
| Amount of the pressure-sensitive adhesive solution (g/m$^2$) | 210 | 200 | 220 | 180 |
| Percent stretch of the tape support (%) | 40 | 30 | 60 | 20 |
| Elongation of the stretchable cloth adhesive tape (%) | 95 | 53 | 138 | 31 |
| Stress at 20% stretch (g/19 mm) | 490 | 320 | 1200 | 290 |
| Fixed feeling after taping | Good | Good | Good | Good |

While the invention has been described in detail and with reference to specific embodiments thereof, it will be apparent to one skilled in the art that various changes and modifications can be made therein without departing from the spirit and scope thereof.

What is claimed is:

1. A stretchable cloth adhesive tape comprising a tape support woven from warps and wefts and having stretchability in one or two directions and a pressure-sensitive adhesive layer formed on one surface of the support, the tape support being fixed by the pressure-sensitive adhesive layer partly biting into the surface of the support in a state stretched at least 3% of said support's maximum elongation upon being stretched to a limit.

2. The stretchable cloth adhesive tape as in claim 1, wherein the wefts are composite yarns composed of a stretchable core and covering fiber yarns wrapped around the core.

3. The stretchable cloth adhesive tape as in claim 2, wherein the core is colored.

4. The stretchable cloth adhesive tape as in claim 2, wherein the core has a size of 20 to 250 denier.

5. The stretchable cloth adhesive tape as in claim 2, wherein the core is composed of polyurethane rubber yarns.

6. The stretchable cloth adhesive tape as in claim 2, wherein the covering fiber yarns have a size of 100 to 500 denier.

7. The stretchable cloth adhesive tape as in claim 1, wherein the count of the warps is 15 to 50 per inch.

8. The stretchable cloth adhesive tape as in claim 1, wherein the wefts have a size of 100 to 500 denier.

9. The stretchable cloth adhesive tape as in claim 1, wherein the count of the wefts is 20 to 100 per inch.

10. The stretchable cloth adhesive tape as in claim 1, wherein the tape support is fixed in a state stretched 5 to 80% of its maximum elongation upon being stretched to the limit.

11. A stretchable cloth adhesive tape as in claim 2 wherein the stretchable core is composed of a synthetic rubber or a synthetic resin.

12. A stretchable cloth adhesive tape as in claim 11 wherein the synthetic rubber is selected from the group consisting of polyurethane rubber and chlorinated rubber, and wherein the synthetic resin is a mixture of polypropylene and ethylene/vinyl acetate copolymer.

13. A stretchable cloth adhesive tape as in claim 3 wherein the color of the core is different from the color of the covering fiber yarns.

* * * * *